United States Patent [19]

Leslie et al.

[11] 4,456,532

[45] Jun. 26, 1984

[54] BIOLOGICAL FLOCCULATION OF MINERAL SLIMES

[75] Inventors: John F. Leslie, Terre Haute, Ind.; Randolph L. Greasham, Mountainside, N.J.; Matthew H. Hulbert, Terre Haute, Ind.

[73] Assignee: International Minerals & Chemical Corp., Terre Haute, Ind.

[21] Appl. No.: 492,984

[22] Filed: May 9, 1983

[51] Int. Cl.$^3$ .................... C02F 3/32; A01G 7/00; C12R 1/89

[52] U.S. Cl. .................... 210/602; 210/611; 210/907; 47/1.4; 435/262; 435/946

[58] Field of Search ............ 210/602, 610, 611, 907, 210/730; 47/1.4, 58; 435/257, 262, 946, 264

[56] References Cited

U.S. PATENT DOCUMENTS

| | | | |
|---|---|---|---|
| 3,406,114 | 10/1968 | Goren | 210/907 |
| 3,684,706 | 8/1972 | Bomstein | 210/907 |
| 3,956,119 | 5/1976 | Davidtz | 210/907 |
| 3,958,364 | 5/1976 | Schenck et al. | 210/602 |
| 4,072,606 | 2/1978 | Leavitt | 210/907 |
| 4,078,332 | 3/1978 | Savins | 435/257 |
| 4,087,936 | 5/1978 | Savins et al. | 47/1.4 |
| 4,236,349 | 12/1980 | Ramus | 47/1.4 |
| 4,331,538 | 5/1982 | Kickuth | 210/602 |

OTHER PUBLICATIONS

G. R. Lanza et al., Studies in Environ. Sci., 19:83–99 (1982).
J. H. Gary et al., Chem. & Phys. Beneficiation of Florida Phosphate Slimes, Report No. 6163; U.S. Bureau of Mines; pp. 33–35.
P. R. Aston et al., Florida Scient. 37:150–155 (1974).

*Primary Examiner*—Benoit Castel
*Attorney, Agent, or Firm*—Robert H. Dewey

[57] ABSTRACT

A process for the consolidation of mineral slimes resulting from the beneficiation of ores comprising the steps of mixing the slimes with a microorganism species or a mixture thereof or ruptured or dried cells thereof, or a fermentation beer on which the organism was grown wherein the organism is selected from the group of cyanobacteria and allowing the mixture to separate into a clear upper layer and a consolidated slimes lower layer.

14 Claims, No Drawings

BIOLOGICAL FLOCCULATION OF MINERAL SLIMES

This invention relates to the beneficiation of ores. In a particular aspect, it relates to an improved process for disposal of wastes resulting from ore beneficiation.

Fine-grained mineral wastes, commonly termed "slimes," are by-products generated in the extraction and beneficiation of phosphate, potash and coal, of petroleum from tar sands, of aluminum from bauxite, and of diamonds from kimberlite. In general, a rapid, economical separation of these slimes from the water used in ore processing is not feasible. A typical problem is that of managing the slimes which result from mining of phosphate rock. To settle the wet slimes produced by the Florida phosphate mining industry alone requires the addition of 1200 hectares per year to the state's 28,000 hectare pond system.

In central Florida the phosphate ore occurs in layers 1 to 3 m thick covered by 3 to 9 m of sandy overburden. Typically the ore consists of approximately one-third phosphate grains and pebbles, one-third quartz sand and one-third slimes (largely clay). This ore is recovered by surface mining and commonly transported as a 40% solids-water slurry. Hydrocyclones separate the slimes fraction from the rest of the ore. Included with the slimes is a fraction of phosphate rock of a size range which accelerates the initial settling. This fraction is potentially recoverable but its removal would exacerbate the slimes-settling problem.

The slimes are discharged into an initial settling pond as an aqueous suspension of 1—5% solids. Settling of the solids can be promoted by addition of chemical flocculants, by mechanical dewatering, or the solids can simply be allowed to settle by gravitation for about six months. When sufficient settling has taken place that the settled layer reaches maximum pumpable density (14–16% solids), the slimes are pumped to final settling ponds. Disposal of the slimes in old mine cuts at grade level is the ideal solution but not generally met in practice since it requires that the water content be reduced from 97% to 66% or less. This final settling may require 20–30 years. Water recovered from the slime is recycled to the beneficiation process; however, approximately one-half of the water used by the industry remains with the slimes.

Microbial enhancement of slimes settling has been proposed by previous investigators, e.g. M. B. Goren, U.S. Pat. No. 3,406,114; R. H. Bornstein, U.S. Pat. No. 3,684,706; J. C. Davidtz, U.S. Pat. No. 3,956,119; F. R. Aston et al, Florida Scient. 37:150-155 (1974); G. R. Lanza et al, Stud. Environ. Sci. 19:83-99 (1982): and J. H. Gary et al, Bureau of Mines Report of Investigation No. 6163 (1962). The proposed processes utilized microbial polysaccharides or nucleoproteins as the flocculating agents and suffered from one or both of these problems: (1) the microbes producing the flocculant required a relatively expensive energy source for growth, and (2) the flocculant required purification before use. Either of these requirements renders the process economically unattractive.

There exists, therefore, a pressing need for an improved method for consolidation of slimes resulting from beneficiation of ores.

SUMMARY OF THE INVENTION

It is an object of this invention to provide an improved process for the beneficiation of ores.

It is another object of this invention to provide an improved process for the disposal of wastes resulting from ore beneficiation processes.

Other objects of this invention will be apparent to those skilled in the art from the disclosure herein.

It is the discovery of this invention to provide a process for accelerating the consolidation of mineral slimes resulting from the beneficiation of ores by mixing the slimes with cells of a cyanobacterium (blue-green algae) species or a mixture thereof, and allowing the slimes to separate into a lower layer leaving a layer of clear water above, which can be periodically withdrawn as needed. It is also an embodiment of this invention to consolidate the slimes by substituting for live cells of a cyanobacterium species the dried or ruptured cells or spent beer on which the organism was grown.

DETAILED DISCUSSION

The process of this invention will be discussed principally with reference to consolidation of slimes from phosphate ore beneficiation. It is understood, however, that the process is not limited to phosphate slimes but instead is applicable to slimes in general, e.g. those resulting from potash and alumina processes.

The improved process comprises the steps of (a) growing the organism in a body of open water, e.g. an existing slimes storage pond, where the cells collect at or near the surface of the water, (b) adding nutrients as needed to promote the growth of the organism, (c) harvesting the cells of the organism after sufficient growth has occurred, (d) delivering the cells to the slimes and mixing well so that the slimes contain a suspension of whole or ruptured cells, (e) subjecting the slimes to an initial dewatering step until maximum pumpable density is reached, and (f) effecting final dewatering of the slimes. Clear water is separated from time to time as appropriate.

Cyanobacteria (blue-green algae) are photoautotrophic organisms which have been studied by R. Rippka et al, J. Gen. Microbiol. 111:1-61 (1969). Typical organisms useful in the practice of this invention include but are not limited to the unicellular *Anacystis nidulans*, the filamentous *Anabaena cylindrica* and species of the Spirulina genus. *A. nidulans* is a particularly preferred species. *A. cylindrica* has the advantageous property of being capable of fixing atmospheric nitrogen in heterocysts. Preferably young cultures of this organism are used. Other cyanobacteria genera useful for the practice of this invention include but are not limited to: Gloeobacter, Gloeothece, Gloeocapsa, Synechococcus, Synechocystis, Chamaesiphon, Dermocarpa, Xenococcus, Dermocarpella, Myxosarcina, Chroococcidiopsis, Pleurocapsa, Hyella, Hydrococcus, Onkonema, Tryponema, Oscillatoria, Pseudanabaena, Plectonema, Phormidium, Schizothrix, Lyngbya, Microcoleus, Azolla, Anabaena, Anacystis, Nodularia, Cylindrospermum, Nostoc, Scytonema and Calothrix.

It is an embodiment of this invention that *A. cylindrica*, as well as other organisms, are advantageously utilized as dried or ruptured cells when delivered to the slimes. The cells can be dried by any suitable means, e.g. they can be freeze dried or simply left in the sun to air dry. Rupture of cells is generally effected by the drying step, or they can be mechanically ruptured. Also, in another embodiment of this invention the organism is cultivated on a nutritive fermentation medium to form a beer having flocculating properties. The beer may be used in place of the organism in the slimes or as a supplement to cells of the organism.

Cultivation of the organism is generally started on a small scale, e.g. by growing it in a seed pond until a good crop is obtained. Then the contents of the pond are used to inoculate a large body of open water, such as a large settling pond. Nutrients such as $CO_2$, trace elements, and fixed nitrogen can be added to the seed pond as needed to enhance growth, if desired.

During the period of growth of the organism in the open body of water, cells of the organism are found at or near the surface where they receive the sunlight needed for growth. When the growth has reached a degree adjudged to be sufficient, the upper layer of water containing the organism may be drawn off for use with the slimes. It is necessary that this layer be well mixed with the slimes, and this can be effected by any suitable means, many of which will be apparent to those skilled in the art. One convenient and preferred method is to add the cells to the water used for ore transport and beneficiation. The extreme agitation, turbulence and grinding action of the ore solids provide thorough mixing and effect mechanical rupture of cells where such is advantageous, as, for example, when *A. cylindrica* is employed. If the latter has been dried, the cells can simply be added to the ore slurry.

The slimes and suspended cells, or fragments thereof, are separated from the phosphate rock in the beneficiation process, and this mixture is then preferably subjected to an initial dewatering step, which can be any dewatering step, many of which are known, e.g. pumping the slimes mixture to a short-term settling pond until maximum pumpable density is reached, e.g. for about 6–12 months; or the slimes can be dewatered by the use of mechanical thickeners such as a rotating trommel screen.

After the slimes have been subjected to an initial dewatering, they are subjected to a final dewatering by any known method, e.g. by pumping the mixture to a final settling pond for long term storage to effect final slimes consolidation.

The invention will be better understood with reference to the following examples. It is understood that these examples are intended only to illustrate the invention and it is not intended that the invention be limited thereby.

EXAMPLE 1

A culture of Anacystis nidulans ATCC 27344 was obtained from the American Type Culture Collection. A seed culture was grown at 26° C. in a 500 ml Erlenmeyer flask by inoculating 100 ml of BG-11 medium (R. Y. Stanier et al, Bacteriol. Rev. 35:171–205). Illumination was provided by cool-white fluorescent lamps providing 400 foot candles.

After two days the culture was added to 2 liters of BG-11 medium to which 400 g of sodium carbonate had been added. The medium was contained in a 4-liter, flat-bottomed, round bottle. This culture was incubated as before except that aeration with a 99% air/1% $CO_2$ mixture was provided at a rate of 1 liter per minute. The culture was harvested by centrifugation at 12,000 g for ten minutes. The cells were then resuspended in 100 ml distilled water and the dry weight per ml was determined. This concentrated cell suspension was used for inoculating slimes.

A quantity of Florida phosphate slimes was obtained from an initial settling pond at a commercial phosphate operation in Noralyn, Fla. The slimes was an 18% solids slurry that was diluted to approximately 3.6% solids before each test.

The effect of the organism on slimes consolidation was measured by adding 5, 10 and 15 ml of the concentrated cell suspension to 10 ml aliquots of the 18% solids slimes in a 125 ml Erlenmeyer flask and diluting to 50 ml, thereby providing an approximately 3.6% solids suspension. Three such suspensions were prepared for each cell concentration. These suspensions, along with a sample of slimes only as a control, were gently mixed on a shaker at room temperature.

After mixing for 0.5, 3.0 and 14.0 hours respectively, the suspensions and control were transferred to 25 ml graduated cylinders and allowed to stand. As the slimes consolidated, a sharp interface appeared between the clear water above and the slimes suspension below. The height of the interface was taken as a measure of the percentage increase in consolidation. The pH remained between 7.1 and 7.6 throughout the test.

The results obtained were plotted on coordinate paper and the following values were interpolated from the curves.

TABLE 1

| | Consolidation After 0.5 Hours Mixing | | | |
|---|---|---|---|---|
| Time Hrs. | Slimes Only % | 1.2 mg algae/ml Algae % | 2.2 mg/ml % | 3.0 mg/ml % |
| 0 | 0 | 0 | 0 | 0 |
| 50 | 151 | 159 | 190 | 95 |
| 100 | 161 | 183 | 211 | 214 |
| 150 | 148 | 191 | 213 | 213 |
| 200 | 174 | 196 | 221 | 219 |
| 250 | 176 | 207 | 233 | 226 |

TABLE 2

| | Consolidation After 3 Hours Mixing | | | |
|---|---|---|---|---|
| Time Hrs. | Slimes Only % | 1.2 mg algae/ml Algae % | 2.2 mg/ml % | 3.0 mg/ml % |
| 0 | 0 | 0 | 0 | 0 |
| 50 | 120 | 144 | 123 | 32 |
| 100 | 154 | 170 | 188 | 200 |
| 150 | 155 | 178 | 198 | 209 |
| 200 | 160 | 183 | 203 | 209 |
| 250 | 164 | 191 | 214 | 222 |

TABLE 3

| | Consolidation After 14 Hours Mixing | | | |
|---|---|---|---|---|
| Time Hrs. | Slimes Only % | 1.2 mg algae/ml Algae % | 2.2 mg/ml % | 3.0 mg/ml % |
| 0 | 0 | 0 | 0 | 0 |
| 50 | 76 | 108 | 45 | 55 |
| 100 | 121 | 148 | 204 | 77 |
| 150 | 122 | 179 | 215 | 79 |
| 200 | 132 | 201 | 220 | 83 |
| 250 | 138 | 203 | 221 | 209 |

On the basis of the foregoing, it was concluded that prolonged mixing had no advantage and that half an hour was adequate. The optimum amount of culture added was 2.2 mg/ml which gave results equally as good as the higher amounts. The settling of the slimes-only control was in every case much slower than the treated samples.

EXAMPLE 2

The experiment of Example 1 was repeated in all essential details except that the organism used was *Anabaena cylindrica* ATCC 29014 at 0.7 mg/ml. Results showed that it was less effective than *A. nidulans* but superior to untreated slimes. With this organism, a half hour period of mixing was satisfactory, but three hours was better.

EXAMPLE 3

To determine if the age of the culture was critical, samples of *A. nidulans* were taken at ages of 3, 6, 8 and 10 days. Slimes were inoculated with 1.2 mg/ml of fresh cells and the suspensions were permitted to stand for 650 hours. No significant differences were observed. It was concluded that the age of the culture was not critical.

EXAMPLE 4

The effect of freeze drying the cultures was tested by freeze drying cells from 300 hour cultures of both *A. nidulans* and *A. cylindrica*. The slimes were treated with 1 mg/ml of dried cells. The interpolated data are given in Table 4. Slimes consolidation was significantly greater in the samples treated with either cyanobacteria than in the untreated control. Surprisingly, the *A. cylindrica* caused considerably more rapid consolidation during the first eight hours than was expected.

TABLE 4

| Time Hrs. | Slimes Consolidation, Dried Cells | | |
|---|---|---|---|
| | Control | A. cylindrica | A. nidulans |
| 0 | 0 | 0 | 0 |
| 1 | 0 | 65 | 1 |
| 5 | 69 | 108 | 72 |
| 10 | 89 | 129 | 89 |
| 25 | 128 | 168 | 131 |
| 50 | 167 | 199 | 174 |
| 100 | 193 | 223 | 212 |
| 150 | 211 | 240 | 234 |
| 200 | 218 | 250 | 246 |

EXAMPLE 5

The experiment of Example 4 is repeated in all essential details except that *A. cylindrica* only is sun dried until it appears to be substantially dehydrated and dry. Slimes consolidation in the presence of the dried cells proceeds much more rapidly than in the control.

EXAMPLE 6

The experiment of Example 4 is repeated in all essential details using Spirulina spp. as the organism. Slimes consolidation in the presence of the dried cells proceeds much more rapidly than in the control.

EXAMPLE 7

*A. nidulans* is cultivated on a nutrient fermentation medium as described in Example 1 and the cells are separated by centrifugation after a suitable growth period. The beer remaining after removal of cells is used for treating slimes, which consolidate much more rapidly than the control.

We claim:

1. A process for the consolidation of mineral slimes resulting from the beneficiation of ores comprising the steps of (a) culturing a microorganism selected from the cyanobacterium group in a body of open water where the cells collect at or near the surface, (b) harvesting the cells after sufficient growth has occurred, (c) delivering the cells to the slimes and mixing well so that the slimes contain a suspension of whole or ruptured cells, (d) subjecting the slimes to an initial dewatering step until maximum pumpable density is reached, and (e) effecting final dewatering of the slimes.

2. The process of claim 1 wherein the microorganism is a species of the genera Anacystis, Anabaena, Spirulina, Gloeocapsa or Nostoc.

3. The process of claim 2 wherein living or dried cells of *A. nidulans* are used as the microorganism.

4. The process of claim 1 wherein dried or ruptured cells are used.

5. The process of claim 4 wherein the cells are those of *A. nidulans*.

6. The process of claim 4 wherein the cells are those of *A. cylindrica*.

7. The process of claim 4 where the cells are those of Spirulina spp.

8. A process for the consolidation of mineral slimes resulting from the beneficiation of ores comprising the steps of (a) culturing a microorganism selected from the cyanobacterium group on a nutritive fermentation medium to form a beer having flocculating properties, (b) separating the beer after sufficient growth has occurred, (c) delivering the beer to the slimes and mixing well, (d) subjecting the slimes to an initial dewatering step until maximum pumpable density is reached, (e) effecting final dewatering of the slimes.

9. The process of claim 8 wherein the microorganism is a species of the genera Anacystis, Anabaena, Spirulina, Gloeocapsa or Nostoc.

10. The process of claim 9 wherein the microorganism is *A. nidulans*.

11. The process of claim 9 wherein the microorganism is *A. cylindrica*.

12. The process of claim 9 wherein the microorganism is a Spirulina spp.

13. The process of claim 1 or 8 wherein the slimes result from the beneficiation of phosphate rock ore.

14. The process of claim 1 or 8 wherein the slimes result from the beneficiation of potash.

* * * * *

UNITED STATES PATENT AND TRADEMARK OFFICE
CERTIFICATE OF CORRECTION

PATENT NO. : 4,456,532
DATED : June 26, 1984
INVENTOR(S) : John F. Leslie et al

It is certified that error appears in the above-identified patent and that said Letters Patent are hereby corrected as shown below:

Table 1, Table 2, Table 3, third column, in the heading,

Cancel "Algae" second occurrence.

Signed and Sealed this

Second Day of April 1985

[SEAL]

*Attest:*

DONALD J. QUIGG

*Attesting Officer*     *Acting Commissioner of Patents and Trademarks*